| United States Patent [19] | [11] Patent Number: 5,061,715 |
| Sunkara et al. | [45] Date of Patent: Oct. 29, 1991 |

[54] PREVENTION OF GLYCOPROTEIN ENVELOPED VIRUS INFECTIVITY BY QUINOLYL- AND ISOQUINOLYLOXAZOLE-2-ZONES

[75] Inventors: Sai P. Sunkara; Winton D. Jones, both of Cincinnati, Ohio

[73] Assignee: Merrell Dow Pharmaceuticals Inc., Cincinnati, Ohio

[21] Appl. No.: 590,523

[22] Filed: Oct. 3, 1990

Related U.S. Application Data

[63] Continuation-in-part of Ser. No. 435,318, Nov. 13, 1989, abandoned.

[51] Int. Cl.$^5$ ............................................. A61K 31/47
[52] U.S. Cl. ................................... 514/314; 514/310
[58] Field of Search ............................... 514/310, 314

*Primary Examiner*—Jerome D. Goldberg
*Attorney, Agent, or Firm*—Stephen L. Nesbitt

[57] ABSTRACT

This invention relates to quinolyloxazole-2-ones which are useful anti-enveloped virus agents by virtue of their ability to act as protein kinase C inhibitors. These derivatives are disclosed to be effective in treating enveloped virus infections including HIV infections and are thus useful in the treatment of AIDS and ARC.

7 Claims, No Drawings

PREVENTION OF GLYCOPROTEIN ENVELOPED VIRUS INFECTIVITY BY QUINOLYL- AND ISOQUINOLYLOXAZOLE-2-ZONES

This is a continuation-in-part of application Ser. No. 07/435,318, filed Nov. 13, 1989, now abandoned.

This invention relates to the use of certain quinolyl- and isoquinolyloxazole-2-ones in the treatment and prevention of infections by enveloped virus including retroviral, e.g., HIV, infections.

BACKGROUND OF THE INVENTION

A great deal of research is currently underway to develop treatments and cures for viral infections in humans and in animals. Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including Kaposi's sarcoma and *Pneumocystis carninii* pneumonia. No cure is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromasomal DNA of the host cell making possible viral replication by later translation of the integrated DNA containing the viral genome.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes, specifically the CD4+ subpopulation, and has been identified as the causative agent of acquired immune deficiency syndrome (AIDS) and AIDS related complex (ARC).

Retroviruses have, in addition to the usual viral capsid, an outer membrane of lipid and glycoprotein, similar to the membrane of ordinary cells. Indeed the lipid of the retroviral membrane is probably derived directly from the membrane of a previously infected host cell, however, the glycoprotein of the viral membrane is unique to the virus itself and is coded for by the viral genome. Infection of a host cell by a retrovirus initially relies on the interaction of various receptors on the host cell surface with the glycoprotein membrane envelope of the virus. Subsequently the virus and cell membranes fuse and the virion contents are released into the host cell cytoplasm. The glycoprotein envelope of the retroviruses plays an important role in both the initial interaction of the virion and the host cell and in the later fusion of the viral and host cell membranes.

In addition to the retroviruses, certain other viruses are coated or enveloped by a glycoprotein layer as well. Such viruses include the herpes simplex viruses (HSV), the influenza viruses, cytomegloviruses (CMG), and others.

Infection of human CD4+ cells by HIV has been shown to involve binding of the HIV gp120 surface protein to a receptor on the surface of the CD4+ cells, the CD4 receptor. Recently it has been observed that binding of HIV to CD4+ cells is accompanied by phosphorylation of CD4 and it has been suggested that this phosphorylation may be protein kinase C (PKC) mediated. Fields, et al., Nature, Vol. 333, May 19, 1988. Experiments indicate that the presence of the PKC inhibitor, 1,5-isoquinolinesulphonyl-2-methylpiperazine dihydrochloride, does not interfere with HIV cell surface binding but causes an accumulation of virus particles at the cell surface and inhibition of viral infectivity, thus supporting the concept that phosphorylation, subsequent to binding, is necessary for infectivity. Applicants have discovered that PKC mediated phosphorylation is important in infectivity of Moloney Murine Leukemia virus (MoLV) as well, and applicants suggest that PKC mediated phosphorylation is an important step in host binding infectivity of enveloped viruses in general.

Applicants have determined that certain quinolyl- and isoquinolyloxazole-2-ones having PKC inhibiting activity are useful in the treatment of various enveloped virus infections including in the treatment of AIDS and ARC resulting from infection by HIV or other retroviruses.

SUMMARY OF THE INVENTION

The present invention is directed to certain quinolyl- and isoquinolyloxazole-2-ones of the formula

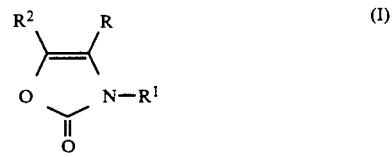

wherein
R and R¹ are each independently selected from the group consisting of hydrogen, $C_1$–$C_6$ alkyl, and phenyl or $C_1$–$C_3$ alkylphenyl wherein the phenyl ring is optionally substituted with one, two or three of the substituents selected from the group consisting of fluorine, chlorine, bromine, $C_1$–$C_4$ alkyl, and $C_1$–$C_4$ alkoxy: and R² is a 2-, 3-, or 4-quinolyl group or a 1-, 3-, or 4-isoquinolyl group wherein the quinolyl or isoquinolyl group is optionally substituted with one, two or three of the substituents selected from the group consisting of fluorine, chlorine, bromine, $C_1$–$C_4$ alkyl, $C_1$–$C_4$ alkoxy, nitro, trifluoromethyl, and phenyl optionally substituted with one, two or three of the substituents selected from the group consisting of fluorine, chlorine, bromine, $C_1$–$C_4$ alkyl, and $C_1$–$C_4$ alkoxy; or R² is a 5-, 6-, 7-, or 8-quinolylor isoquinolyl group; and to the pharmaceutically-acceptable salts thereof.

DETAILED DESCRIPTION OF THE INVENTION

This invention concerns the use of the compounds of Formula I as agents effective in the treatment of infections of enveloped viruses.

As used herein, the terms "$C_1$–$C_3$ alkyl", "$C_1$–$C_4$ alkyl" and "$C_1$–$C_6$ alkyl" mean straight or branched chain alkyl groups having from one to three, from one to four, or from one to six carbon atoms respectively, and include such groups as methyl, ethyl, n-propyl, isopropyl, n-butyl, isobutyl, sec-butyl, tert-butyl, and the like, as well as vinyl, allyl, propynyl, butenyl, butadienyl, isopropenyl, and the like. The term "$C_1$–$C_4$ alkoxy" means alkoxy groups having from one to four carbon atoms, and includes such groups as methoxy, ethoxy, n-propoxy, isopropoxy, n-butoxy, isobutoxy, sec-butoxy, tert-butoxy, and the like. When R or $R^1$ is "optionally substituted $C_1$–$C_3$ alkylphenyl", the one, two or three substituent(s) can be located at any available position on the phenyl ring. When $R^2$ is 2-, 3-, or 4-quinolyl or 1-, 3-, or 4-isoquinolyl the optional substituent(s) can be located at any available position(s) on the quinolyl or isoquinolyl ring.

The expression "a pharmaceutically acceptable acid addition salt" is intended to apply to any non-toxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Illustrative examples of the compounds of this invention include compounds of Formula I wherein the R groups are designated as follows:

| R | $R^1$ | $R^2$ |
| --- | --- | --- |
| hydrogen | hydrogen | 2-, 3-, or 4-quinolyl |

| R | $R^1$ | $R^2$ |
| --- | --- | --- |
| ethyl | hydrogen | 2-, 3-, or 4-quinolyl |
| propyl | hydrogen | 5-, 6-, 7- or 8-quinolyl |
| methyl | benzyl | 2-, 3- or 4-quinolyl |
| phenethyl | hydrogen | 2-, 3- or 4-quinolyl |
| propyl | hydrogen | 2-, 3- or 4-(6, 7-dimethyl)-quinolyl |
| propyl | hydrogen | 2-, 3- or 4-(6-phenyl)-quinolyl |
| 4-methoxyphenethyl | hydrogen | 2, 3- or 4-quinolyl |
| 4-methoxyphenyl | hydrogen | 2, 3- or 4-quinolyl |
| benzyl | benzyl | 2-, 3- or 4-(7-ethoxy)-quinolyl |
| benzyl | benzyl | 2-, 3- or 4-(7-ethoxy)-quinolyl |
| phenyl | phenyl | 2-, 3- or 4-(7-phenyl)-quinolyl |
| butyl | hydrogen | 2-, 3- or 4-quinolyl |
| 3,5-dichloro)phenylpropyl | methyl | 5-, 6-, 7- or 8-quinolyl |
| 3,5-dichloro)phenyl | methyl | 5-, 6-, 7- or 8-quinolyl |
| propyl | methyl | 2-, 3- or 4-quinolyl |
| 3,5-dimethoxybenzyl | ethyl | 5-, 6-, 7- or 8-quinolyl |
| 3,5-dimethoxyphenyl | ethyl | 5-, 6-, 7- or 8-quinolyl |
| methyl | propyl | 2-, 3- or 4-(5-ethoxy-7-methyl)-quinolyl |
| methyl | propyl | 2-, 3- or 4-(5-phenyl)-quinolyl |
| butyl | butyl | 5-, 6-, 7- or 8-quinolyl |
| hydrogen | phenethyl | 2-, 3- or 4-(6-trifluoromethyl)-quinolyl |
| hydrogen | phenyl | 2-, 3- or 4-(6-trifluoromethyl)-quinolyl |
| hydrogen | phenethyl | 2-, 3- or 4-(6-phenyl)-quinolyl |
| methyl | 4-methoxyphenethyl | 2-, 3- or 4-quinolyl |
| methyl | 4-methoxyphenyl | 2-, 3- or 4-quinolyl |

Equivalently substituted isoquinolyl derivatives are also intended. As is true for most classes of therapeutically effective compounds, certain subclasses and certain species which are especially effective are preferred over others. In this instance, those compounds of Formula I wherein $R^2$ is optionally substituted 2-, 3-, or 4-quinolyl are preferred. Also preferred are compounds wherein R is $C_1$–$C_6$ alkyl, as well as compounds wherein $R^1$ is hydrogen. Most preferred are the compounds wherein $R^2$ is an unsubstituted 2-, 3-, or 4-quinolyl group, R is ethyl or propyl and $R^1$ is hydrogen.

The 2-, 3-, or 4-quinolyloxazole-2-ones of this invention can readily be prepared by the reaction depicted in Reaction Scheme 1.

Reaction Scheme 1

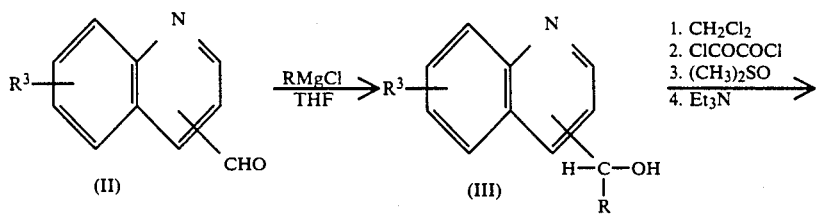

-continued
Reaction Scheme 1

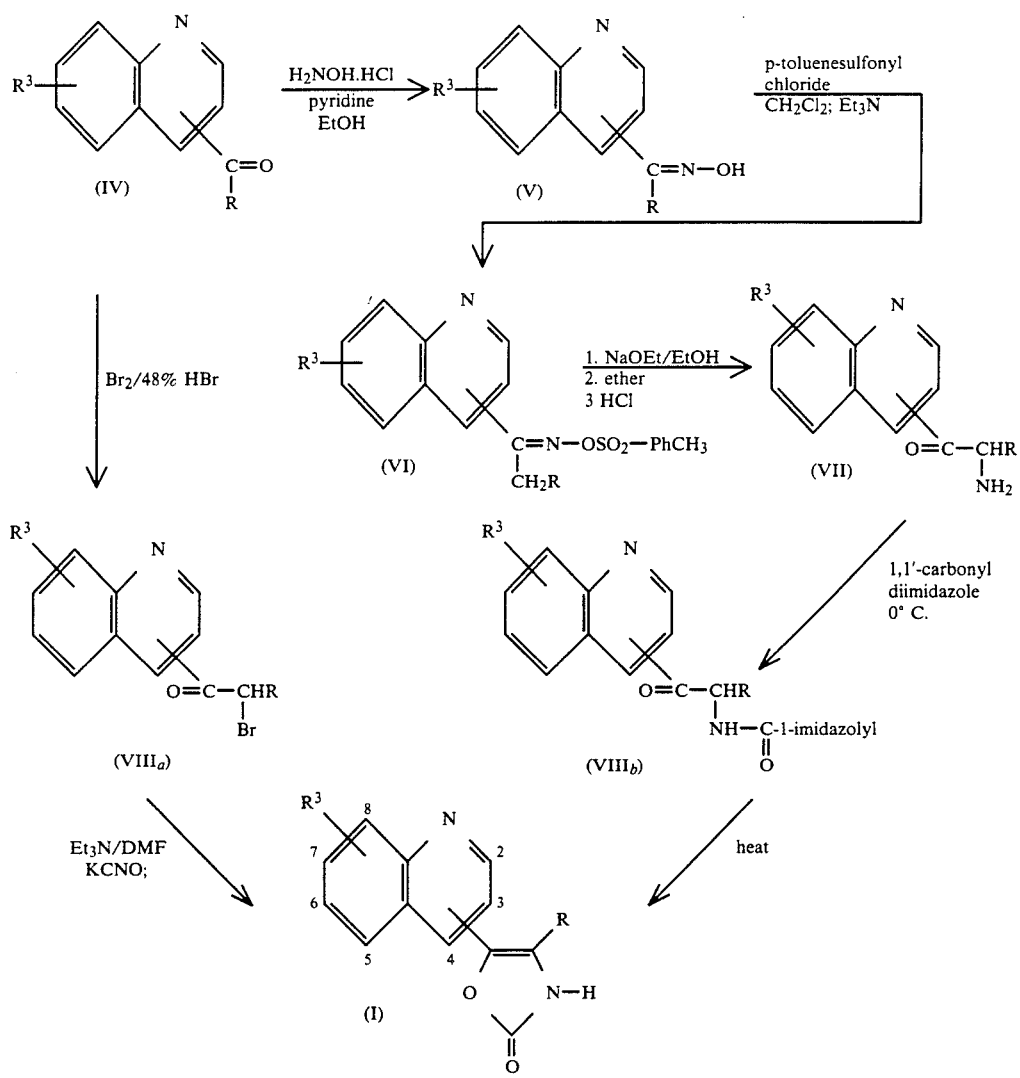

wherein R is as in Formula I, R³ is the optional R² group substituent(s) of Formula I, and other symbols are as defined hereinafter.

In essence, Reaction Scheme 1 illustrates that the 2-, 3-, or 4-quinolyloxazole-2-ones of Formula I can be prepared by reacting the appropriate and readily available 2-, 3-, or 4-quinoline carboxaldehyde (II) in tetrahydrofuran (THF) with alkylmagnesium chloride or with optionally substituted phenylalkyl-magnesium chloride [RMgCl] to produce 2-, 3-, or 4-quinoline alkanol (III), which is in turn oxidized with oxalyl chloride (ClCOCOCl), methyl sulfoxide [$(CH_3)_2SO$] and triethylamine ($Et_3N$) in dichloromethane ($CH_2Cl_2$) to produce quinolyl-alkanone (IV). The alkanone (IV) can alternately be brominated to compound (VIII$_a$) and further treated with triethylamine in dimethylformamide (DMF) in the presence of potassium cyanate (KCNO) to form the compounds of Formula I according to procedures well known in the art and illustrated in the examples herein; or compound IV can be converted to oxime (V) by refluxing with hydroxylamine hydrochloride ($H_2NOH.HCl$) and pyridine in ethanol (EtOH). Compound (V) is then reacted with p-toluenesulfonyl chloride and triethylamine in dichloromethane to produce compound (VI). The amine (VII) is then produced by reacting compound (VI) with sodium ethoxide in ethanol (NaOEt/EtOH), followed by ether and aqueous hydrochloric acid (HCl) extraction. The amine (VII) is further reacted with 1,1'-carbonyldiimidazole at about 0° C. to form compound (VIII$_b$), which is then heated to about 170° C. to yield the appropriate 2-, 3-, or 4-quinolyloxazole-2-ones of Formula I. The unsubstituted 5-, 6-, 7- or 8-quinolyloxazole-2-ones of this invention can readily be prepared by the reaction depicted in Reaction Scheme 2.wherein R is as in Formula I, R³ is the optional R² group substituent of Formula I, and other symbols are as defined for Reaction Scheme 1.

The unsubstituted 5-, 6-, 7- or 8-quinolyloxazole-2-ones of this invention can readily be prepared by the reaction depicted in Reaction Scheme 2.

Reaction Scheme 2

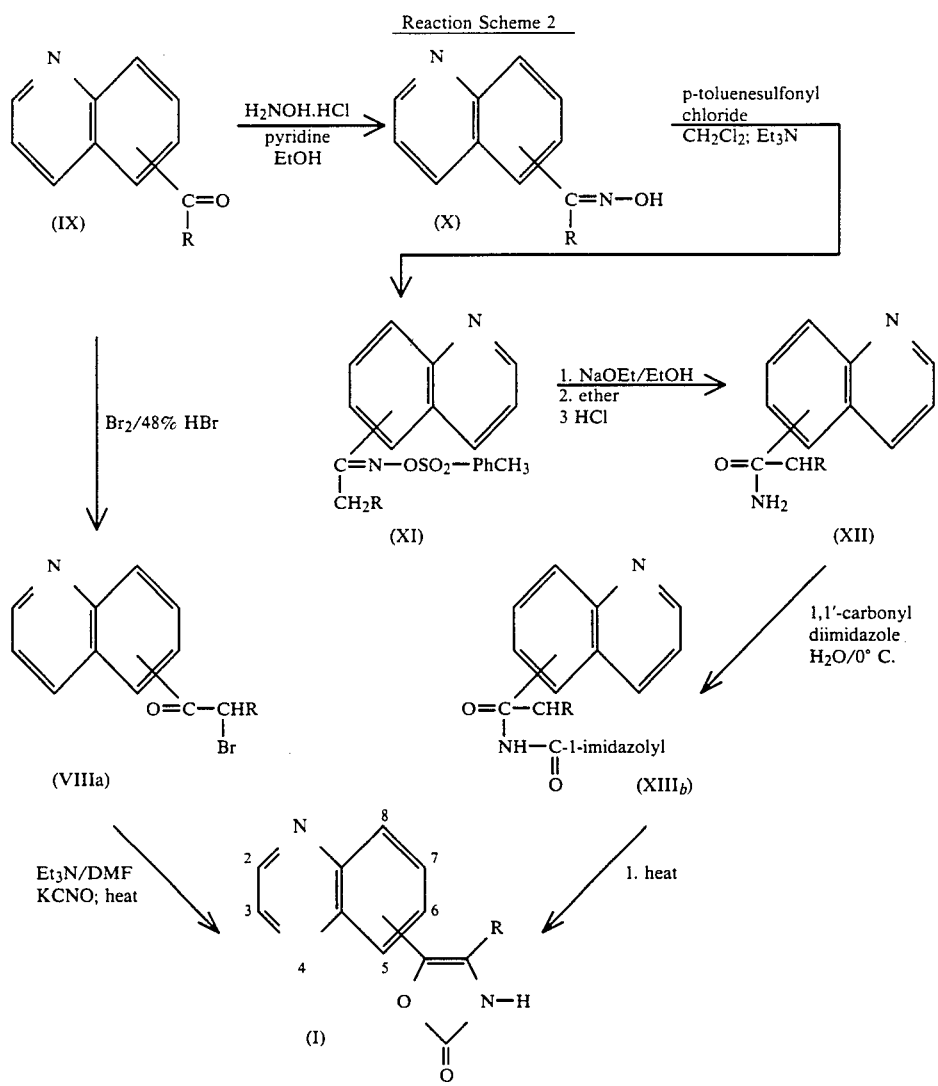

wherein R is as in Formula I, R³ is the optional R² group substituent of Formula I, and other symbols are as defined for Reaction Scheme 1.

In essence, Reaction Scheme 2 illustrates that the 5-, 6-, 7-, or 8-quinolyloxazole-2-ones of Formula I can be prepared in essentially the same manner as described for Reaction Scheme 1. The alkanone starting material (IX) is prepared by metalating 5-, 6-, 7- or 8-bromoquinoline according to a procedure by H. Gilman and T. Suddy set forth in *J. Org. Chem.* 23, 1584–9 (1958), and then reacting it with N-alkoxy-N-alkylamides. The 5-, 6-, 7-, or 8-bromoquinoline compounds are prepared by following procedures set forth in "The Chemistry of Heterocyclic Compounds" by Gurnos Jones, as found in *Quinolines*, Part 1, vol. 32, p. 100–117 and 247–258, ed. A. Weissberger and E. C. Taylor, John Wiley and Sons, London, 1977. These procedures can also be utilized for preparing 2-,3-, or 4-bromoquinolines and their corresponding 2-, 3-, or 4-quinolinyl alkanones such as those of formula (IV) in Reaction Scheme 1.

Alternatively, the formula (IV) and formula (IX) compounds of Reaction Schemes 1 or 2 can also be prepared by reacting the appropriate bromoquinoline with butyl lithium in an appropriate solvent such as THF or diethyl ether at −70° C. to 0° C., preferably at −50° C., and then reacting the lithiated compound with

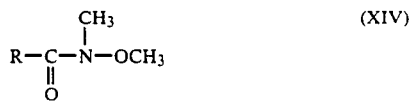

(XIV)

wherein R is as described in Formula I. This reaction is further specifically exemplified in Example 8. Compound (XIV) can be prepared by a procedure set forth in *Tetrahedron Letters*, 22, 3815 (1981).

The compounds wherein $R^1$ is $C_1$-$C_6$ alkyl or optionally substituted $C_1$-$C_3$ alkylphenyl are produced by subsequent reaction of the compound of Formula I of either Reaction Scheme 1 or Reaction Scheme 2 with sodium hydride and the appropriate alkyl iodide or phenylalkyl iodide in tetrahydrofuran according to procedures well known in the art.

Likewise, one of ordinary skill will readily be able to modify these procedures to obtain isoquinoline derivatives of formula 1.

The ability of the oxazolone derivatives of this invention to act as anti-enveloped virus agents can be demonstrated by their ability to inhibit the growth and replication of murine leukemia virus, an oncogenic retrovirus, as determined by an in vitro XC plaque assay. This assay was performed according to the method of Rowe et al. (*Virology,* 1970, 42, 1136–39) as previously described by L. Hsu, et al (*J. Virological Methods,* 1980, 1, 167–77) and T. L. Bowlin and M. R. Proffitt (*J. Interferon Res.,* 1983, 3(1), 19–31). Mouse SC-1 cells (fibroblast) ($10^5$) were seeded into each well of 6-well cluster plates (Costar #3506) in 4 ml Minimum Essential Medium (MEM) with 10% Fetal Calf Serum (FCS). Following an 18 hour incubation period (37° C.), Moloney murine leukemia virus (MoLV) was applied at a predetermined titer to give optimal (i.e. countable) numbers of virus plaques. Compounds were added 2 hours prior to addition of the virus. Three days later the culture medium was removed, the SC-1 cell monolayers were exposed to UV irradiation (1800 ergs), and rat XC cells ($10^6$) were seeded into each well in 4 ml MEM. Following an additional 3 day incubation (37° C.), these cells were fixed with ethyl alcohol (95%) and stained with 0.3% crystal violet. Plaques were then counted under low magnification. The antiviral activity of the compound of this invention, 4-propyl-5-(4-quinolinyl)-2(3H)-oxazolone is tabulated in Table 1.

TABLE 1

ANTIRETROVIRAL ACTIVITY OF 4-PROPYL-5-(4-QUINOLINYL)-2(3H)-OXZAOLONE AGAINST MOLONEY MURINE LEUKEMIA VIRUS (MoLv) IN CULTURE

| Compound | Concentration (μg/ml) | Mean No. of Foci | % Inhibition |
|---|---|---|---|
| Control | | 84 | |
| Test Compound | 1 | 10 | 88.1 |
| | 0.10 | 84 | 0 |

The ability of the oxazolone derivatives of this invention to act as anti-enveloped virus agents can be demonstrated by their ability to reduce expression of p24 antigen from HIV infected T-lymphocytes. Cells (C8166 T cell line) were pretreated with test compounds at appropriate concentrations for 3 hours prior to virus (RF strain of HIV-1) absorption. Low multiplicity of infection was used and virus absorption period was 1 hour at room temperature. the cells were washed Xl in PBS and resuspended in fresh medium containing the appropriate concentrations of test compound. Cells incubated at 37° C. and after 3 days culture fluid was assayed for p24 antigen as a measure of viral replication. Because these compounds were insoluble in water as their free base, they had to be taken up in DMSO and therefore a series of DMSO virus controls were needed for comparison.

TABLE 2

ANTI-HIV ACTIVITY OF 4-PROPYL-5-(4-QUINOLINYL)-2(3H)OXAZOLONE

| Compound | Concentration (μg/ml) | Vehicle (DMSO) % | p24 Antigen (pg/ml) | % Inhibition |
|---|---|---|---|---|
| Vehicle (DMSO) | | 0.1 | 2408 | |
| Control | | 0.1 | 1027 | |
| Test Compound | 10 | 0.1 | 710 | 71 |
| | 1 | 0.01 | 745 | 28 |

The oxazolone derivatives of this invention can be used to treat a number of diseases and conditions known to be caused by enveloped viruses including those diseases and conditions caused by murine leukemia virus, feline leukemia virus, cytomegalovirus (CMV), avian sarcoma virus, herpes simplex virus (HSV), invluenza virus, human immunodeficiency virus (HIV), HTLV-I, and HTLV-II. Those experienced in this field are readily aware of the circumstances requiring anti-enveloped virus therapy. Applicants consider the use of the oxazolone derivatives of this invention to treat HIV infections in humans to be of most importance. The term "patient" used herein is taken to mean mammals such as primates, including humans, sheep, horses, cattle, pigs, dogs, cats, rats and mice.

The amount of the oxazolone derivative of formula 1 to be administered can vary widely according to the particular dosage unit employed, the period of treatment, the age and sex of the patient treated, the nature and extent of the disorder treated, and the particular oxazolone derivative selected. Moreover the oxazolone derivative can be used in conjunction with other agents known to be useful in the treatment of enveloped virus diseases and agents known to be useful to treat the symptoms of and complications associated with diseases and conditions caused by enveloped viruses. The anti-enveloped virally effective amount of a oxazolone derivative of formula 1 to be administered will generally range from about 15 mg/kg to 500 mg/kg. A unit dosage may contain from 25 to 500 mg of the oxazolone derivative, and can be taken one or more times per day. The oxazolone derivative can be administered with a pharmaceutical carrier using conventional dosage unit forms either orally or parenterally.

The preferred route of administration is oral administration. For oral administration the oxazolone derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc, stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The oxazolone derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene-glycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be use din the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the oxazolone derivative of formula 1 in solution. Preservatives and buffers may also be used advantageously. In order to minimize or eliminate irritation at the site of injection, such compositions may contain a nonionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol. The following specific examples are presented to illustrate the synthesis of the compounds of this invention, but they should not be construed as limiting the scope of this invention in any way.

EXAMPLE 1

1-Butyl-4-Quinoline Methanol (III)

In a liter, 3-necked flask equipped with a mechanical stirrer, dropping funnel, reflux condenser (all dried under argon), and thermometer, were placed 15.0 grams (0.0954 M) of 4-quinoline carboxaldehyde and 400 ml of dry tetrahydrofuran (THF). The mixture was cooled by means of stirring in a dry ice/methanol bath to −70° C. Butylmagnesium chloride (100 ml of 2 M) was added through the funnel at a fast drop rate over a period of about 45 minutes, and the mixture was allowed to stir at −70° C. for about an hour. Then, 100 ml saturated ammonium chloride (NH$_4$Cl) was added dropwise through the funnel and the mixture was allowed to warm to room temperature whereupon the resulting semi-solid material was filtered off under vacuum and washed with about 100 ml THF. The THF layers were combined and washed with saturated sodium chloride solution and then dried over magnesium sulfate. The inorganic matter was filtered off by vacuum through diatomaceous earth and the solvent evaporated. The residue was flash chromatographed on silica (1:1 ethyl acetate/hexane) and, after evaporation of the solvent, about 5.0 gram of purified title compound was recovered.

EXAMPLE 2

1-(4-Quinolinyl)-1-Pentanone (IV)

In a 1 liter, 3-necked flask equipped with a mechanical stirrer, dropping funnel, reflux condenser (all dried under argon), and thermometer, were placed 50 ml of dry dichloromethane and 3.79 ml (0.043 M) oxalyl chloride. The resulting mixture was stirred in a dry ice/methanol bath to maintain a temperature of −70° C. Methyl sulfoxide (6.17 ml, 0.043 M) was added dropwise and subsequently a solution of 9.26 grams (0.043 M) of the compound of Example 1 in dry dichloromethane (CH$_2$Cl$_2$) was added and the mixture allowed to stir cold for about 15 minutes. Triethylamine (35.6 ml) was then added and the mixture was allowed to stir cold for about 1 hour. After the mixture had been allowed to warm to room temperature, it was poured into a flask containing about 600 ml water. The CH$_2$Cl$_2$ layer was separated and the aqueous layer extracted with CH$_2$Cl$_2$ (2 times, 100 ml each). The combined CH$_2$Cl$_2$ layers were washed with saturated sodium chloride and dried over magnesium sulfate. The inorganic matter was filtered off and the solvent evaporated leaving a residue that was flash chromatographed as in Example 1. Evaporation left 9.0 grams of title compound.

EXAMPLE 3

1-(4-Quinolinyl)-1-Pentanone Oxime (V)

In a 500 ml, 3-necked flask equipped with a mechanical stirrer, dropping funnel, reflux condenser (all dried under argon), were placed 8.3 grams (0.03892 M) of the compound of Example 2, 4.12 grams (0.0584 M) of hydroxylamine hydrochloride, 40 ml of dry pyridine, and about 200 ml of dry ethanol. The mixture was refluxed for 6 hours, then the solvent was evaporated leaving a residue which was treated with about 400 ml ether and 200 ml water. The ether layer was separated and washed several times with water, washed with saturated sodium chloride and dried over magnesium sulfate. The inorganic matter was filtered off and the solvent evaporated, leaving 8.42 grams (94.7%) of the title compound.

EXAMPLE 4

1-(4-Quinolinyl)-1-Pentanone-0-[(4-Methylphenyl)Sulfonyl] Oxime (VI)

In a 250 ml erhlenmeyer flask filled with argon were placed 8.42 grams (0.0369 M) of the compound of Example 3 and about 130 ml dry CH$_2$Cl$_2$. While stirring and cooling to about 0° C. in an ice/methanol bath, about 20 ml of triethylamine was added over a 5 minute period, then 10.55 grams (0.0554 M) toluenesulfonyl chloride was added and the mixture allowed to stir for 3 hours. The solution was then evaporated to dryness which left a residue that was treated with ether and water. The ether phase was separated and the water phase extracted twice more with ether. The combined ether layers were extracted with dilute sodium hydroxide, washed with saturated sodium chloride and dried over magnesium sulfate. The inorganic matter was filter off using vacuum, and the solvent was evaporated leaving 15.1 grams of the title compound.

EXAMPLE 5

2-Amino-1-(4-Quinolinyl)-1-Pentanone (VII)

In a 250 ml, 3-necked flask equipped with a mechanical stirrer, dropping funnel, reflux condenser (all dried under argon), was placed 60 ml dry ethanol. While stirring, 2.55 grams (0.111 M) of sodium spheres were added and allowed to continue to stir under argon until the sodium dissolved. A solution of 15.1 grams of the compound of Example 4 in ethanol was then added and the mixture stirred for 4 hours at room temperature. The mixture was then poured into a flask containing 1200 ml absolute ether. The resulting precipitate was filtered off under vacuum through diatomaceous earth, and the filtrate extracted with 2N hydrochloride acid (3 times, 170 ml each). The extract was evaporated leaving 19.8 grams of the title compound.

EXAMPLE 6

N-[2-Oxo-1-Propyl-2-(4-Quinolinyl)Ethyl]-1H-Imidazole-1-Carboxamide (VIII$_b$)

The compound of Example 5 (19.8 grams) was dissolved in about 300 ml water, and the solution filtered by gravity into a 1 liter, 3-necked flask equipped with a mechanical stirrer and a thermometer. The solution was cooled to 0° C. with stirring in an ice/methanol bath, and 29.87 grams (0.185 M) 1,1'-carbonyldiimidazole was added over a 5 minute period. The mixture was allowed to stir cold for about 15 minutes. The resulting precipitate was taken up in about 500 ml ethyl acetate and separated from the water. The solution was washed with saturated sodium chloride and dried over magnesium sulfate, and the inorganic matter filtered off using diatomaceous earth under vacuum. The solvent was evaporated leaving the title compound.

EXAMPLE 7

4-Propyl-5-(4-Quinolinyl)-1-(3H)-Oxazolone (I)

The compound of Example 6 (12 grams) was heated under vacuum to 170° C. for about 30 minutes, allowed to cool to room temperature and washed with water. The water was decanted and the residue was treated with $CH_2Cl_2$ (20 ml). The $CH_2Cl_2$ was evaporated leaving 7.8 grams of residue. The product was purified by means of flash chromatography on silica, eluting with ethyl acetate. The solvent was evaporated and the residue dissolved in 48 ml hot 50% ethanol, filtered and allowed to cool to room temperature. The precipitate was collected by vacuum filtration and dried in vacuo at 78° C., leaving 1.97 grams (21%) title compound. M.p. 188°-190° C. dec.; analysis calced. for $C_{15}H_{14}N_2O_2$: C, 70,85; H, 5.55; N, 11.02; analysis found: C, 71.10; H, 5.73; N, 10.76.

EXAMPLE 8

1-(3-Quinolinyl)-1-butanone

In a dry 3-necked flask under argon at −50° C., n-butyl lithium (0.0025 M, 0.021 ml) was added to 150 ml diethylether. Then 4.16 grams 3-bromoquinoline in 2 ml THF was added dropwise while stirring and maintaining the temperature at −60° C. to −55° C. The solution was stirred for 30 minutes, and 2.3 grams N-methyl-N-methoxybutyramide were then added dropwise at −50° C. and the solution was stirred an additional 30 minutes. The solution was then allowed to warm to 0° C. and stirred for one hour. The reaction was quenched with a saturated solution of ammonium chloride and the THF layer separated, washed with brine, separated, and dried over magnesium sulfate. Filtration through diatomaceous earth, followed by concentration and subsequent thin layer chromatography (35% ethylacetate/65% $CH_2Cl_2$) gave a total yield of 2.03 g (51%) of the title compound.

By substituting the following starting materials for the 4-quinoline carboxaldehyde and/or the butylmagnesium chloride of Example 1, and following the procedures set forth in Examples 1 through 7, the following end products can be made in a like manner.

A. 6- or 8-methoxy-4-quinoline carboxaldehyde and methylmagnesium chloride, to yield 5-(6- or 8-methoxy-4-quinolinyl)-1-(3H)-oxazolone B. 2-quinololine carboxaldehyde and methylmagnesium chloride, to yield 5-(2-quinolinyl)-1-(3H)-oxazolone C. 7- or 8-chloro-4-quinoline carboxaldehyde and propylmagnesium chloride, to yield 4-ethyl-5-(7- or 8-chloro-4-quinolinyl)-1-(3H)-oxazolone D. 6,8-dichloro or dibromo-4-quinoline carboxaldehyde and butylmagnesium chloride, to yield 4-propyl-5-(6,8-dichloro or dibromo-4-quinolinyl)-1-(3H)-oxazolone E. 7- or 8-nitro-4-quinoline carboxaldehyde and pentylmagnesium chloride, to yield 4-butyl-5-(7- or 8-nitro-4-quinolinyl)-1-(3H)-oxazolone F. 7-trifluoromethyl-4-quinoline carboxaldehyde and hexylmagnesium chloride, to yield 4-pentyl-5-(7-trifluoromethyl-4-quinolinyl)-1-(3H)-oxazolone G. 5,8-dimethoxy-4-quinoline carboxaldehyde and benzylmagnesium chloride, to yield 4-phenyl-5-(5,8-dimethoxy-4-quinolinyl)-1-(3H)-oxazolone H. 5,8-dimethoxy-6-nitro-4-quinoline carboxaldehyde and ethylmagnesium chloride, to yield 4-methyl-5-(5,8-dimethoxy-6-nitro-4-quinolinyl)-1-(3H)-oxazolone I. 6-methoxy-8-nitro-4-quinoline carboxaldehyde and propylmagnesium chloride, to yield 4-ethyl-5-(6-methoxy-8-nitro-4-quinolinyl)-1-(3H)-oxazolone J. 5,6-dimethoxy-8-nitro-4-quinoline carboxaldehyde and pentylmagnesium chloride, to yield 4-butyl-5-(5,6-dimethoxy-8-nitro-4-quinolinyl)-1-(3H)-oxazolone K. 5-methyl-4-quinoline carboxaldehyde and benzylmagnesium chloride, to yield 4-phenyl-5-(5-methyl-4-quinolinyl)-1-(3H)-oxazolone L. 2-(4-methoxy)phenyl-4-quinoline carboxaldehyde and 3,5-dimethoxybenzymagnesium chloride, to yield 4-(3,5-dimethoxyphenyl)-5-[1-(4-methoxyphenyl)-4-quinolinyl]-1-(3 H)-oxazolone M. 6,8-dimethoxy-4-quinoline carboxaldehyde and 4-methylbenzylmagnesium chloride, to yield 4-(4-methylphenyl)-5-(6,8-dimethoxy-4-quinolinyl)-1-(3H)-oxazolone N. 4-quinolinecarboxaldehyde and propylmagnesium chloride, to yield 4-ethyl-5-(4-quinolinyl)-1(3H)-oxazolone (mp 273–76° C.)

O. 4-quinolinecarboxaldehyde and pentylmagnesium chloride, to yield 4-butyl-5-(4-quinolyl-1(3H)-oxazolone (mp 196–98° C.)

P. 3-quinolinecarboxaldehyde and butylmagnesium chloride, to yield 4-propyl-5-(3-quinolyl)-1(3H)-oxazolone (mp 193–95° C.)

Q. 4-isoquinolinecarboxaldehyde and butylmagnesium chloride to yield 4-propyl-5-(4-isoquinolyl)-1(3H)-oxazolone (mp 122-24° C.)

By substituting 1-(3-quinolinyl)-1-pentanone for the compound of Example 2 and by following the procedure set forth in Examples 3 through 7, 4-propyl-5-(3-quinolinyl)-(3H)-oxazolone is produced.

In a like manner, by substituting the following starting materials for 1-(4-quinolinyl)-1-pentanone of Example 2 and following the procedure set forth in the preceding paragraph, the following end products can be made.

R. 1-(5-quinolinyl)-1-pentanone, to yield 4-propyl-5-(5-quinolinyl)-1-(3H)-oxazolone S. 1-(6-quinolinyl)-1-butanone, to yield 4-ethyl-5-(6-quinolinyl)-1-(3H)-oxazolone T. 1-(7-quinolinyl)-1-ethanone, to yield 5-(7-quinolinyl)-1-(3H)-oxazolone U. 1-(8-quinolinyl)-1-phenylethanone, to yield 4-phenyl-5-(8-quinolinyl)-1-(3H)-oxazolone V. 1-(5,8-dimethoxy-3-quinolinyl)-1-propanone, to yield 4-methyl-5-(5,8-dimethoxy-3-quinolinyl)-1-(3H)-oxazolone.

The following specific examples are presented to illustrate compositions of this invention, but they should not be construed as limiting the scope of this invention in any way.

EXAMPLE 9

A tablet is prepared from

| 4-Methyl-5-(3-quinolinyl)-1-(3H)-oxazolone | 250 mg |
|---|---|
| Starch | 40 mg |
| Talc | 10 mg |
| Magnesium | 10 mg |

EXAMPLE 10

A capsule is prepared from

| 4-phenyl-5-(2-quinolinyl)-1-(3H)-oxazolone | 400 mg |
|---|---|
| Talc | 40 mg |
| Sodium Carboxymethy celulose | 40 mg |
| Starch | 120 mg |

The compounds of Formula I may also be utilized, in free base form or in compositions, in research and diagnostics, or as analytical references or standards, and the like. Therefore, the present invention includes compositions which are comprised of an inert carrier and an effective amount of a compound of Formula I, or a salt thereof. An inert carrier is any material which does not interract with the compound to be carried and which lends support, means of conveyance bulk, traceable material, and the like to the compound to be carried. An effective amount of compound is that amount which produces a result or exerts an influence on the particular procedure being performed.

It should be apparent to one of ordinary skill in the art that changes and modifications can be made to this invention without departing from the spirit or scope of the invention as it is set forth herein.

What is claimed is:

1. A method of treating an enveloped viral infection in a patient in need thereof which comprises administering to the patient an anti-enveloped virally effective amount of a compound of the formula

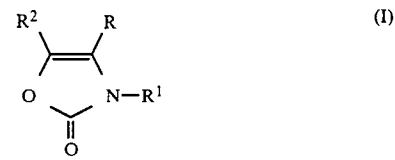

wherein

R and $R^1$ are each independently selected from the group consisting of hydrogen, $C_1$-$C_6$ alkyl, and phenyl or $C_1$-$C_3$ alkylphenyl wherein the phenyl ring is optionally substituted with one, two or three of the substituents selected from the group consisting of fluorine, chlorine, bromine, $C_1$-$C_4$ alkyl, and $C_1$-$C_4$ alkoxy; and $R^2$ is a 2-, 3-, or 4-quinolyl group or 1-,3-, or 4-isoquinolyl group, optionally substituted with one, two or three of the substituents selected from the group consisting of fluorine, chlorine, bromine, $C_1$-$C_4$ alkyl, $C_1$-$C_4$ alkoxy, nitro, trifluoromethyl and phenyl optionally substituted with one, two or three of the substituents selected from the group consisting of fluorine, chlorine, bromine, $C_1$-$C_4$ alkyl, and $C_1$-$C_4$ alkoxy, or $R^2$ is a 5-, 6-, 7-, or 8-quinolyl or isoquinolyl group; or a pharmaceutically-acceptable salt thereof.

2. A method of claim 1 wherein $R^2$ is a 5-, 6-, 7-, or 8-quinolyl group.

3. A method of claim 1 wherein $R^2$ is an optionally substituted 2-, 3-, or 4-quinolyl group.

4. A method of claim 3 wherein R and $R^1$ are each independently selected from the group consisting of hydrogen or $C_1$-$C_6$ alkyl.

5. A method of claim 4 wherein R is $C_1$-$C_6$ alkyl and $R^1$ is hydrogen.

6. A method of claim 3 wherein $R^2$ is an unsubstituted 2-, 3-, or 4-quinolyl group.

7. A method of claim 6 wherein $R_2$ is 4-quinolinyl, R is propyl, and $R^1$ is hydrogen.

* * * * *